United States Patent
Moore et al.

(10) Patent No.: US 9,712,934 B2
(45) Date of Patent: Jul. 18, 2017

(54) SYSTEM AND METHOD FOR CALIBRATION AND REPRODUCTION OF AUDIO SIGNALS BASED ON AUDITORY FEEDBACK

(71) Applicants: Joseph Harold Moore, Nashville, TN (US); Stephen Rhett Davis, Nashville, TN (US)

(72) Inventors: Joseph Harold Moore, Nashville, TN (US); Stephen Rhett Davis, Nashville, TN (US)

(73) Assignee: EARIQ, INC., Nashville, TN (US)

( * ) Notice: Subject to any disclaimer, the term of this patent is extended or adjusted under 35 U.S.C. 154(b) by 0 days.

(21) Appl. No.: 14/801,423

(22) Filed: Jul. 16, 2015

(65) Prior Publication Data

US 2016/0050507 A1 Feb. 18, 2016

Related U.S. Application Data

(60) Provisional application No. 62/025,349, filed on Jul. 16, 2014.

(51) Int. Cl.
*H04R 29/00* (2006.01)
*G06F 3/16* (2006.01)
(Continued)

(52) U.S. Cl.
CPC ............ *H04R 29/00* (2013.01); *A61B 5/123* (2013.01); *G06F 3/162* (2013.01); *H03G 3/02* (2013.01);
(Continued)

(58) Field of Classification Search
CPC .......... A61B 5/123; H04R 3/00; H04R 29/00; H04R 1/1008; H04R 1/1041; H04R 25/70;
(Continued)

(56) References Cited

U.S. PATENT DOCUMENTS 4,773,094 A 9/1988 Dolby
6,078,669 A 6/2000 Maher
(Continued)

OTHER PUBLICATIONS

International Search Report in International Application No. PCT/US2015/040801, dated Oct. 29, 2015, 2 pp.

*Primary Examiner* — Brenda Bernardi
(74) *Attorney, Agent, or Firm* — Patterson Intellectual Property Law, P.C.; Gary L. Montle

(57) ABSTRACT

Systems and methods are provided for testing an individual's hearing and correcting audio signals to compensate for the significant variance in each listener's sensitivity to various frequencies of the audible spectrum. An auditory calibration procedure includes identifying a first volume level as a minimum volume level at which nominal frequency tones are audible, a minimum frequency at which said first volume level is audible, a maximum frequency at which said first volume level is audible, and a minimum volume level at which a number of intervening sample frequencies are audible. A substantially parabolic correction curve is generated based on the minimum volume levels at the various sample frequencies. The correction curve is applied to modify real time audio signals generated upon execution of an audio file functionally linked to the processor, wherein the modified real time audio signals are provided to an audio output device.

20 Claims, 8 Drawing Sheets

(51) Int. Cl.
  *H03G 3/02* (2006.01)
  *H04R 3/00* (2006.01)
  *A61B 5/12* (2006.01)
  *H04R 1/10* (2006.01)
  *H04R 25/00* (2006.01)

(52) U.S. Cl.
  CPC ............. *H04R 3/00* (2013.01); *H04R 1/1008* (2013.01); *H04R 1/1041* (2013.01); *H04R 25/70* (2013.01); *H04R 2430/01* (2013.01); *H04R 2430/03* (2013.01); *H04R 2499/11* (2013.01); *H04R 2499/15* (2013.01)

(58) Field of Classification Search
  CPC ............ H04R 2430/03; H04R 2499/11; H04R 2499/15; H04R 2430/01; G06F 3/162; H03G 3/02
  See application file for complete search history.

(56) References Cited

U.S. PATENT DOCUMENTS

| | | | |
|---|---|---|---|
| 7,181,297 B1 | 2/2007 | Pluvinage et al. | |
| 7,564,979 B2 * | 7/2009 | Swartz | A61B 5/121 |
| | | | 381/312 |
| 8,014,549 B2 | 9/2011 | Kates | |
| 8,059,833 B2 | 11/2011 | Koh et al. | |
| 8,081,768 B2 * | 12/2011 | Steinbuss | A61B 5/121 |
| | | | 381/312 |
| 8,144,881 B2 | 3/2012 | Crockett et al. | |
| 8,300,849 B2 * | 10/2012 | Smirnov | H03G 7/007 |
| | | | 381/104 |
| 8,358,786 B2 | 1/2013 | Arora | |
| 8,503,703 B2 | 8/2013 | Eaton et al. | |
| 8,594,345 B2 | 11/2013 | Hess | |
| 9,087,506 B1 | 7/2015 | Kraft et al. | |
| 2005/0201574 A1 | 9/2005 | Lenhardt | |
| 2006/0045281 A1 * | 3/2006 | Korneluk | A61B 5/121 |
| | | | 381/60 |
| 2006/0078140 A1 | 4/2006 | Goldstein | |
| 2008/0044034 A1 | 2/2008 | Hou | |
| 2008/0254753 A1 * | 10/2008 | Steenstra | H04R 5/04 |
| | | | 455/90.1 |
| 2010/0290653 A1 | 11/2010 | Wiggins et al. | |
| 2011/0040205 A1 | 2/2011 | Parra et al. | |
| 2011/0081029 A1 | 4/2011 | Hashimoto et al. | |
| 2011/0137111 A1 | 6/2011 | Hanley et al. | |
| 2012/0063616 A1 * | 3/2012 | Walsh | H03G 5/025 |
| | | | 381/103 |
| 2012/0189130 A1 * | 7/2012 | Lee | A61B 5/121 |
| | | | 381/60 |
| 2012/0224720 A1 | 9/2012 | Naito | |
| 2012/0300964 A1 | 11/2012 | Ku et al. | |
| 2012/0321112 A1 | 12/2012 | Schubert et al. | |
| 2013/0003981 A1 | 1/2013 | Lane | |
| 2013/0041490 A1 * | 2/2013 | Leonard | H04R 3/04 |
| | | | 700/94 |
| 2013/0188813 A1 | 7/2013 | Waldmann | |
| 2014/0024914 A1 | 1/2014 | Fadem | |
| 2014/0072132 A1 * | 3/2014 | Gautama | H03G 3/345 |
| | | | 381/71.1 |
| 2014/0153754 A1 | 6/2014 | Moesgaard et al. | |
| 2014/0169573 A1 | 6/2014 | Terrel et al. | |
| 2014/0192992 A1 | 7/2014 | Lee et al. | |
| 2014/0194775 A1 | 7/2014 | Van Hasselt et al. | |
| 2014/0198935 A1 | 7/2014 | Moesgaard et al. | |
| 2014/0236043 A1 * | 8/2014 | Coninx | A61B 5/123 |
| | | | 600/559 |
| 2014/0254828 A1 * | 9/2014 | Ray | H03G 5/165 |
| | | | 381/103 |
| 2014/0279787 A1 | 9/2014 | Cheng et al. | |
| 2014/0309549 A1 | 10/2014 | Selig et al. | |
| 2014/0314261 A1 | 10/2014 | Selig et al. | |
| 2014/0334644 A1 | 11/2014 | Selig et al. | |
| 2015/0078575 A1 | 3/2015 | Selig et al. | |

\* cited by examiner

SYSTEM AND METHOD FOR CALIBRATION AND REPRODUCTION OF AUDIO SIGNALS BASED ON AUDITORY FEEDBACK

CROSS-REFERENCES TO RELATED APPLICATIONS

This application claims benefit of U.S. Provisional Application No. 62/025,349, filed Jul. 16, 2014, and which is hereby incorporated by reference.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present disclosure relates generally to systems and methods for improving audio output. More particularly, the present disclosure relates to systems and methods for testing an individual's hearing and then correcting an audio signal to compensate for that user's unique auditory signature.

The goal of perfect audio reproduction is to record and playback the source material as faithfully to the original as is possible. A perfect audio reproduction would represent the entire spectrum of audible frequencies at the exact same reference volume level. Audio engineers create master recordings that match reference standards so that all audio frequencies at the same signal level represented on a properly mastered recording match that same standard signal level. This is known as a "flat" or "level" reproduction. To record, reproduce, deliver and playback sound, many steps, many devices, and many conversions, are involved. Each of these steps introduces errors biasing the audible spectrum away from perfectly level.

However, while various conventional methods and devices attempt to correct for and restore the audio signal to the reference standard ("equalize" the signal) at different points in the reproduction chain, such methods fail to account for the listener's own ears. As there is significant variance in each individual listener's sensitivity to the various frequencies of the audible spectrum, and this variance increases as the individual listener's hearing is damaged through exposure and age, any method of equalization that does not account for the listener's ears is inadequate for producing an audio signal that matches the reference signal heard by the recording engineer.

BRIEF SUMMARY OF THE INVENTION

Various embodiments of a system and method as disclosed herein may generally be employed to correct for and restore audio signals to a reference standard ("flat" or "level" reproduction") at the final point of audio throughput—the listener's own ears. Such a system may desirably account for the significant variance in each listener's sensitivity to various frequencies of the audible spectrum.

In one aspect of a particular embodiment of a system as disclosed herein may be to utilize a computer interface presented on a desktop or notebook computer, phone or tablet, mobile audio player or integrated with a home, auto or portable audio device, to lead the listener through a calibration process.

Another aspect of a particular embodiment of a system as disclosed herein may be to provide a powerful and user-friendly interface for executing a testing and calibration procedure. The system may for example allow listener to test each ear independently. The system may present a recommended set of frequency sample sizes or allow the listener to enter a custom sample size. Calibration instructions may in some exemplary embodiments be presented visually, audibly or both, and may provide the listener the opportunity to correct a possibly erroneous sample if a given sample deviates unexpectedly from adjacent samples. The system may allow the listener to repeat the calibration process multiple times to generate a mathematical mean and eliminate spurious samples.

Another aspect of a particular embodiment of a calibration process as disclosed herein may be to capture a number of data points that represent the difference between the levels that the listener hears and the desired reference levels. The system may calculate test frequency sample points evenly between the listener's signal floor (lowest audible frequency) and the listener's signal ceiling (highest audible frequency).

Such a calibration process may in various embodiments further generate a mathematical equation representing a parametric curve between data sample points. In some embodiments, an exemplary system may instruct the listener to name and save his or her customized parametric curve, or correction.

Another aspect of a particular embodiment of a system as disclosed herein may be to apply a customized correction to audio signals to correct for the difference between the listener levels and the reference levels. Such system correction can be applied in real time to an audio signal as it is played, and further in certain embodiments can be used to create and save a new version of an audio recording so that the corrected recording can be played back on any device. For example, the system may allow the listener to apply the correction on devices that support the creation of new audio recordings.

Another aspect of a particular embodiment of a system as disclosed herein may be to report the results of the listener's test to a central repository for analysis, or allow the listener to instead opt-out of test data collection. In certain embodiments, such analysis may enable the system to determine that the listener's hearing is severely damaged at specific frequencies and may notify the listener of the results.

Another aspect of a particular embodiment of a system as disclosed herein may be to allow the listener to apply other audio signal transformations including higher sample rates, removing digital compression artifacts, normalizing volume levels, expanding or compressing dynamic range and other transformations.

In a particular embodiment, a non-transitory computer readable medium is functionally linked to an audio output device configured to produce audio output responsive to audio input signals. Program instructions residing on the medium are executable by a processor to direct the performance of operations. Upon initiation of an auditory calibration procedure, a first volume level is identified as a minimum volume level at which a tone having a nominal frequency is audible to a user, a minimum frequency is identified at which a tone at said first volume level is audible to the user, a maximum frequency is identified at which the tone at said first volume level is audible to the user, and for each of one or more samples having frequencies between said minimum frequency and said maximum frequency, a minimum volume level is determined at which a respective frequency is audible to the user. Upon completion of the auditory calibration procedure, a transform equation is generated representing a substantially parabolic correction curve based on the minimum volume levels at each of the nominal frequency, the minimum frequency, the maximum frequency and the one or more sample frequencies. The transform equation is applied to modify real time audio signals generated upon execution of an audio file functionally linked to the processor, wherein the modified real time audio signals are provided as audio input signals to the audio output device.

DETAILED DESCRIPTION OF THE INVENTION

Figure 1:
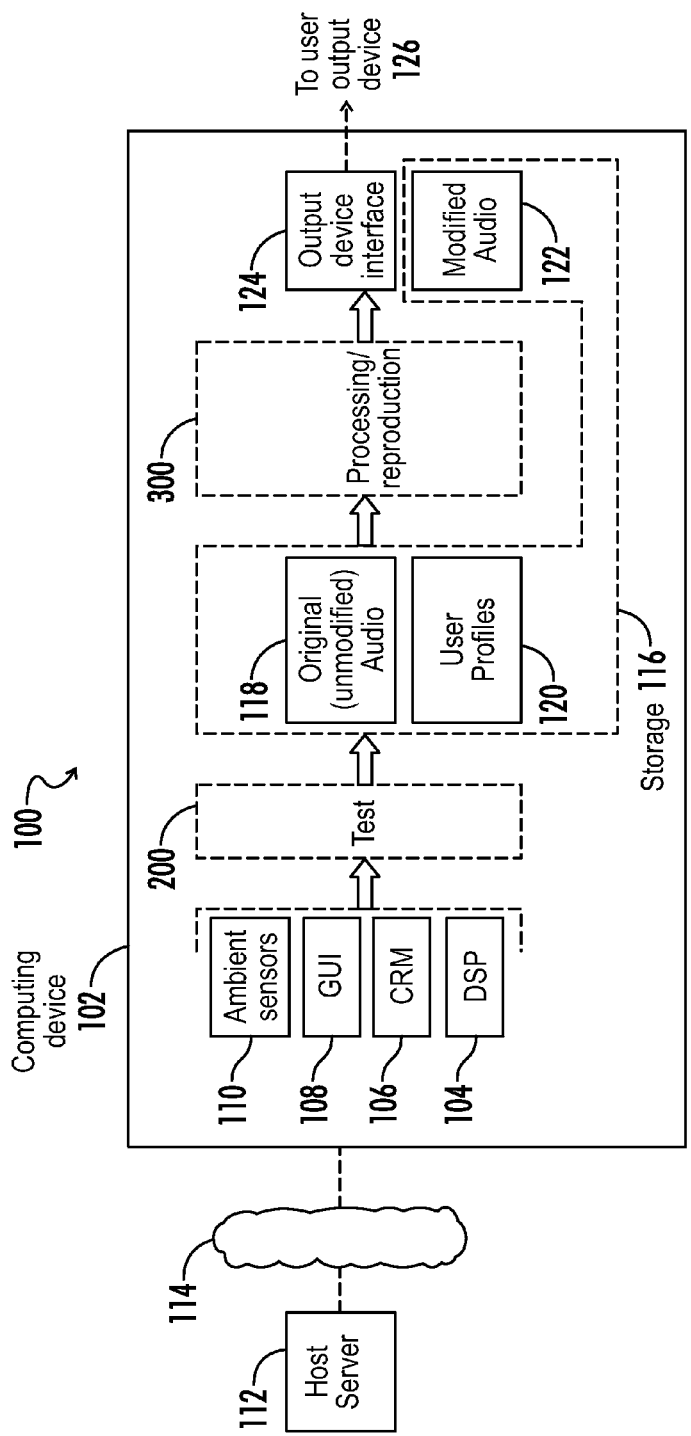
FIG. 1 includes a block diagram representing an embodiment of a system according to the present disclosure.

Referring generally to FIGS. 1-4, various exemplary embodiments of an invention may now be described in detail. Where the various figures may describe embodiments sharing various common elements and features with other embodiments, similar elements and features are given the same reference numerals and redundant description thereof may be omitted below.

Referring initially to FIG. 1, an embodiment of a system 100 for calibrating an audio signal for optimal sound reproduction leads the end user (i.e., listener) through a step-by-step process that results in the capture of a number of data points that represent the difference between the levels that the listener hears and the desired reference levels. The system then applies a calculation to the audio signal to correct for these differences. This correction can either be applied in real time to the signal as it is played or can be used to create a new version of the sound recording with the correction pre-applied so that the corrected recording can be played back on any device.

In one embodiment the system may include computer program products or modules which can be installed on an end user's device 102 such as a desktop or notebook computer, phone or tablet, mobile audio player or integrated with a home, auto or portable audio device. The system may be installed as a stand-alone application or as part of a companion music application (e.g.—iTunes, Pandora, Rdio, Spotify or even a system and method as disclosed in U.S. Pat. No. 8,549,402 B2.

The end user may install the application in a variety of ways, including, but not limited to, downloading it from a host server 112 via a communications network 114, including the application as part of an update from one or more of the previously identified companion music applications or receiving the application pre-installed with the purchase of a new computer, phone, tablet, mobile audio player or portable audio device. The term "communications network" as used herein with respect to data communication between two or more parties or devices, or otherwise between communications network interfaces associated with two or more parties or devices, may refer to any one of, or a combination of any two or more of, telecommunications networks (whether wired, wireless, cellular or the like), a global network such as the Internet, local networks, network links, Internet Service Providers (ISP's), and intermediate communication interfaces.

The system 100 as disclosed herein may accordingly be referred to as including, or alternatively as residing upon and executable in association with, a computing device 102 and associated components including for example and without limitation one or more data processors 104, and one or more computer-readable media 106 upon which software products, code snippets, executable modules and the like may reside for execution by the processor. The device 102 may typically include a display unit upon which a graphical user interface 108 may be generated for at least input/output features as enabled or otherwise required by the systems and methods as disclosed herein. Ambient condition sensors 110 such as for example microphones may be provided for the purpose of detecting background noise, although the sensors may not be limited to such and may further typically include low voltage signal transceivers, location sensors, temperature sensors, accelerometers, gyroscopes or the like for the execution of any number of peripheral steps or features as may complement or supplement the methods explicitly described herein.

A system as disclosed herein may be configured to execute a testing procedure 200 to for example calibrate subsequently generated audio output signals with respect to a user's specific auditory characteristics. The system may be particularly useful when calibrating a single-user audio output device 126 such as for example headphones, but can also generate meaningful results with any audio reproduction system with sufficient dynamic range and frequency response.

Figure 2:
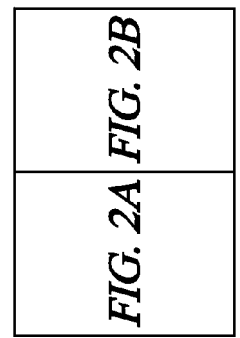
FIGS. 2A and 2B include a flowchart representing an embodiment of a user testing method according to the present disclosure.
Figure 2A:
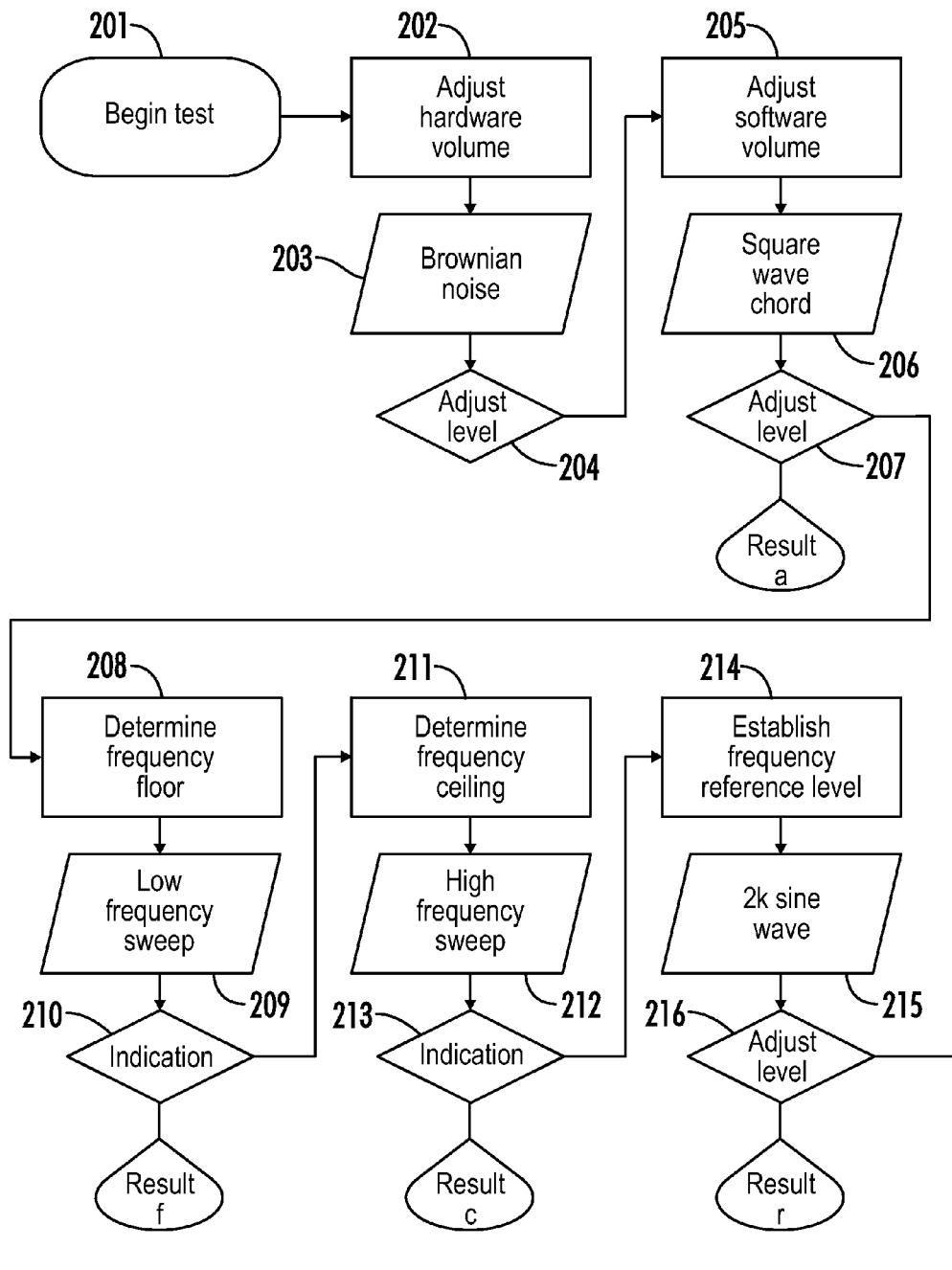
Figure 2B:
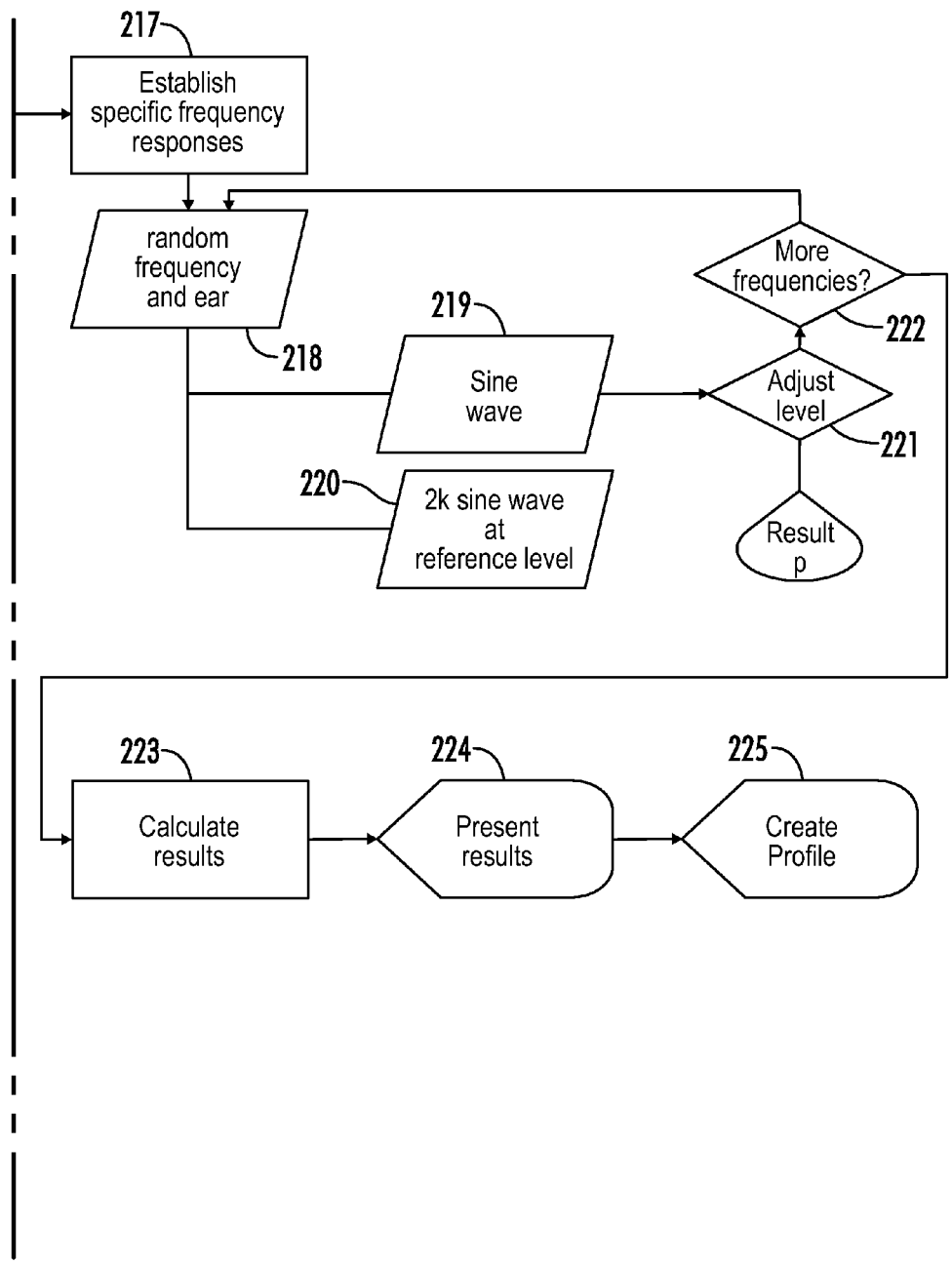
Figure 4:
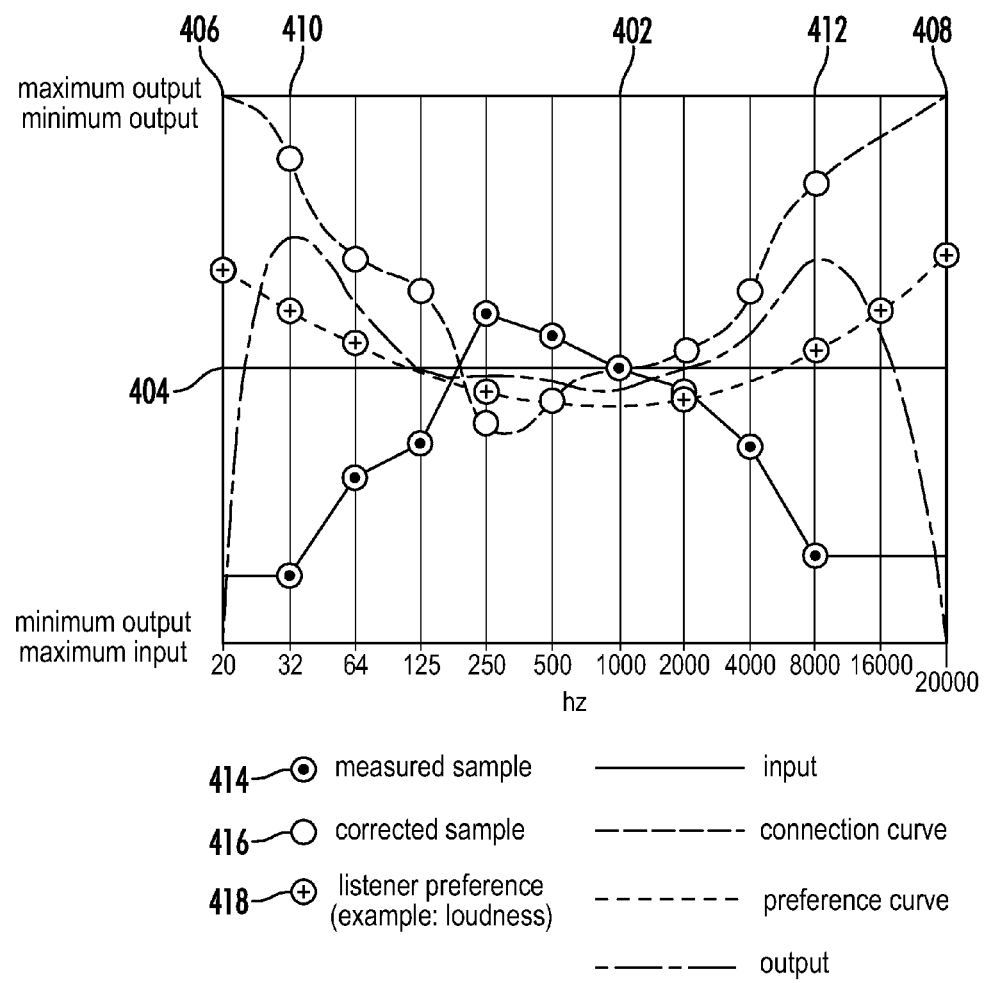
FIG. 4 includes a graphical diagram representing sample data points based on user preferences, wherein an exemplary parametric correction curve is generated to achieve customized and optimal sound reproduction.

Referring more particularly now to FIGS. 2A, 2B and 4, in one embodiment an exemplary testing procedure 200 as described herein may desirably establish "safe" (audible and without distortion) frequency and amplitude limits, and further establishing a maximum "practical" dynamic range as a subset of the "theoretical" maximum dynamic range of the signal, both by reference to frequency as well as amplitude.

Beginning with step 201, the user may be prompted to find a quiet area, and further to adjust their output device (e.g., headphones) according to any relevant manufacturer's recommendations. The user may further be prompted to adjust the output device's volume control to a nominal relative position such as for example its middle position.

In various embodiments, the system may enable the user to indicate the thoroughness of the test they wish to take. For example, the listener may be prompted to pick how many data points (audible frequencies) they wish to sample. The prompts may be presented either visually, audibly, or both. The more frequencies that are tested, the more accurate the resulting sample and thus sound reproduction. As few as three equally distributed frequencies can provide adequate results. There is no upper maximum number of frequencies that can be tested, but more than 128 samples provide diminishing returns, and at a certain point the number of samples would exceed the practical resolution of the recording format or exceed the margin of error in the listener's ability to differentiate between audible frequencies. The system may present a set of recommended sample sizes.

The method of indication may be to indicate one of multiple levels (i.e. quick, average, long). Alternately the method may be to indicate the number of frequencies to be tested (3, 6, 14 or 30).

In accordance with step 202, in one embodiment the user may be prompted by the system to adjust the output device's volume control as loud as they can comfortably listen, or until they hear signal distortion. A sample of Brownian noise may be played at 100% (software) volume, equally applied in both the left and right channel simultaneously (step 203). Alternatively, this portion of the test can be performed individually for each channel (ear). The system enables the user to indicate when the output device's volume control is at their preferred level (step 204).

One of skill in the art may appreciate that the human brain has evolved to be exceptionally good at pattern recognition and at filtering and synthesizing large amounts of raw input. These same abilities make it challenging to accurately test a user's hearing. Therefore, an exemplary testing procedure as described herein may take steps to fight anticipation and assumption, including for example avoiding cues, utilizing random delays before starting playback each test signal, and randomly selecting which frequencies to test. The system may further withhold visual indications of results from the user, implementing "stateless" controllers whenever possible, or otherwise indicating progress as a broad indicator of the present state of the overall test, but without indicating state within an individual step of the overall test.

In embodiments where the listener is enabled to decide if they wish to test each ear independently, the system may further randomize the selection of which ear will be tested for each iteration of frequency testing.

In accordance with steps 205-206, the system may prompt the user to adjust a software (i.e., via the GUI) volume control until the tone is either uncomfortably loud or they hear signal distortion. A sample of a square wave chord, comprised of a low, middle and high frequency tone, may be played at 50% (software) volume, for example at equal volume in both the left and right channel simultaneously. Alternatively, this portion of the test can be performed individually for each channel (ear).

The user may be presented with a graphic user interface volume control that does not reveal the absolute volume level. The user may accordingly use this control to increase or decrease the volume of the sample, but again, the control gives no visual indication of the indicated volume.

In various embodiments, the system may enable the user to indicate that they are ready to proceed or that they wish to retake this portion of the test. When the user is ready to proceed, the chosen maximum software volume level is recorded. The precision of measured volume level can vary depending on the capabilities of the hardware device, but the result is represented and stored at the maximum precision of system, typically 16 bit precision (65,535 values).

In accordance with steps 208-209, a frequency floor may be determined by the system. With further illustrative reference to FIG. 4, the listener may further be presented with an audible tone at reference level (e.g., 50% of the indicated preferred maximum volume, or alternatively 0 db) 404 that "sweeps" upward starting at the lowest audible frequency (e.g., 20 Hz) 406 and proceeding towards a highest audible frequency (e.g., 20 kHz) 408. The listener may be prompted to indicate as soon as the listener can hear the tone (step 210), and the system records or otherwise documents this point 418. In an embodiment, the first frequency that the listener is able to hear serves as the reference "floor" 410 for the final correction, wherein no frequencies below this floor are further tested. If the signal floor is higher than 20 Hz, the final correction will zero levels at 20 Hz and raise them to the signal floor in a logarithmic curve (a natural sounding "roll-off").

In an exemplary embodiment, the listener is instructed to indicate in a manner appropriate for the given testing device (a button press, the tap on a touch screen, etc.) as soon as the listener hears the test tone. The listener is given the opportunity to try again if they feel they made a mistake. This ability to make corrections is also available at each subsequent step.

The user according to one embodiment may be presented with a graphic user interface control that does not reveal the frequency of the tone that is being played. The frequency sweep may increase over a fixed period of time, or in another implementation may be directly controlled by the user. The tone at each frequency may be played at equal volume in both the left and right channel simultaneously, or alternatively this portion of the test can be performed individually for each channel (ear).

The user according to one embodiment may indicate that they are ready to proceed or that they wish to retake this portion of the test. When the user is ready to proceed, the chosen frequency floor (the lowest frequency that the user can hear) is recorded. The precision of measured frequency can vary depending on the capabilities of the audio output device, but the result is represented and stored at the maximum precision of system, typically 16 bit precision (65,535 value).

In accordance with steps 211-212, a frequency ceiling may be determined by the system, wherein the listener may be presented with an audible tone at a reference level (e.g., 50% of the indicated preferred maximum volume, or alternatively 0 db) 404, that "sweeps" downward starting at the highest audible sine wave frequency (e.g., 20 kHz) 408 and theoretically ending with the lowest audible sine wave frequency (e.g., 20 Hz) 406, and the listener is further prompted to indicate as soon as the listener can hear the tone 418. The first frequency that the listener is able to hear serves as the reference "ceiling" 24 for the final correction (step 213). In various embodiments, no frequencies above this ceiling will be further tested. If the signal ceiling is lower than 20 kHz, the final correction may zero levels at 20 kHz and lower them to the signal ceiling 412 in a logarithmic curve.

The user according to one embodiment may be presented with a graphic user interface control that does not reveal the frequency of the tone that is being played. The frequency sweep may increase over a fixed period of time, or in another implementation may be directly controlled by the user. The tone at each frequency may be played at equal volume in both the left and right channel simultaneously, or alternatively this portion of the test can be performed individually for each channel (ear).

The user according to one embodiment may indicate that they are ready to proceed or that they wish to retake this portion of the test. When the user is ready to proceed, the chosen frequency floor (the highest frequency that the user can hear) is recorded. The precision of measured frequency can vary depending on the capabilities of the audio output device, but the result is represented and stored at the maximum precision of system, typically 16 bit precision (65,535 values).

In accordance with steps 214-215, a reference frequency volume level may be determined by the system, wherein in one embodiment a 2 kHz sine wave reference tone 402 may be played at zero volume and increased towards maximum volume (step 216). The level that the listener is able to hear the tone serves as the reference frequency volume level.

The user according to one embodiment may be presented with a graphic user interface control that does not reveal the volume of the tone that is being played. The volume may be increased over a fixed period of time, or in another implementation may be directly controlled by the user. The tone may be played at equal volume in both the left and right channel simultaneously, or alternatively this portion of the test can be performed individually for each channel (ear).

The user according to one embodiment may indicate that they are ready to proceed or that they wish to retake this portion of the test. When the user is ready to proceed, the chosen reference frequency volume (the lowest volume level in which the user can hear the tone) is recorded. The precision of measured frequency can vary depending on the capabilities of the audio output device, but the result is represented and stored at the maximum precision of system, typically 16 bit precision (65,535 values).

At this point, based on the data collected so far, the system may calculate the optimum number of samples to test and present this recommendation to the listener. The listener is free to ignore this recommendation and test as many or as few samples as they desire. A minimum of two additional tones are required for a basic profile. Six, fourteen and thirty tones take more time to test, but allow for progressively more accurate representation of the user's hearing. Based on the number of samples the listener has indicated they wish to test, the system calculates the sample points evenly between the signal floor and the signal ceiling.

In accordance with steps 217-222, and for each of the determined number of sample points, in one particular embodiment the system plays a tone at the respective frequency starting at minimum volume and gradually increasing to maximum volume. For each sample point 414, the listener is instructed to indicate as soon as they can hear the test tone 418. This is repeated for the indicated number of samples 414, and for each ear if that option has been indicated. At each step, the listener has the opportunity to re-do the step to correct for a mistake. The listener is not presented with a visual indication of the volume level in order to not bias their reaction.

In another embodiment, the system plays the tone at the respective frequency being tested, with the volume increasing from 0% (step 219), but also simultaneously plays the 2 kHz sine wave reference tone at 50% of the indicated preferred maximum volume in the channel to be tested (step 220). The user may accordingly be prompted to indicate when the tone at the respective frequency being tested is the same volume as the reference tone (step 221).

The system may typically continue to repeat steps 218-221 as many times as necessary to test the user across the indicated number of frequencies in both the left and right channels. After testing every sample point, the listener may choose to finish the test process, or may choose to do the entire process again. The user according to one embodiment may be presented with a graphic user interface control that does not reveal the volume of the tone that is being played. The volume may be increased over a fixed period of time, or in another implementation may be directly controlled by the user. The precision of measured frequency can vary depending on the capabilities of the audio output device, but the result is represented and stored at the maximum precision of system, typically 16 bit precision (65,535 values).

In accordance with step 223, the results may next be calculated by the system. In one embodiment, the results of multiple tests are averaged to generate a mathematical mean, eliminating spurious samples. If four or more tests are completed, the high and low result for each sample point is removed before averaging in order to eliminate type one (incorrect rejection of a true null) and type two (failure to reject a false null) statistical errors.

In an embodiment, the system may generate a score as an indicator of how close a user's hearing is to the theoretical ideal. The absolute difference from the tested level and actual level of each sample point may be scored on a scale of one (100% deviation) to zero (0% deviation). The total number of sample scores are averaged and multiplied by 200 to arrive at a user's initial or preliminary score. The same method may be used to rate the difference from the actual level of each corrected point and arrive at the user's final score. The score may be used as an indicator of an individual's relative before and after improvement, the relative differences between different loudspeakers, and the relative differences between users.

For example, the calculated differences of the results from steps 207, 210 and 213 (labeled as a, f and c, respectively) are combined by averaging (step 223*a*). The calculated differences of the results from steps 216 and 221 (labeled as r and p, respectively) are combined by averaging (step 223*b*). The results from the various iterations of steps 217-221 may be identified as p(l,r)xxxx wherein p indicates the volume, l or r indicates the channel (ear), and xxxx indicates the frequency for the respective iteration. In this embodiment, the results of step 223*a* and step 223*b* may be further averaged (step 223*c*), wherein the result of step 223*c* is inverted and then normalized on a scale from 70 to 200. This is the user's unaided, or un-corrected test score.

Test results for amplitude ceiling, and frequency floor and ceiling are used to determine the maximum dynamic range available for signal correction. Within these limits, the possible corrected results are calculated for each tested frequency for each tested channel (223*d*). The absolute difference between the corrected results of each step and the theoretical perfect result is calculated and normalized on a scale from 0 to 1 (223*e*). Frequencies outside the measured frequency floor or ceiling are scored as 1 (maximum deviation), and the calculated difference of each corrected frequency is averaged (223*f*). The results of step 223*a* and step 223*f* are averaged, inverted, and then normalized on a scale from 70 to 200. This is the user's aided, or corrected score.

In accordance with step 224, the user may be presented with the results of their test. The results may be presented in a variety of ways, including but not limited to a numerical representation of their before (uncorrected) and after (corrected) scores, or a graph plotting the user's test results against the theoretical maximum.

During the test, the system may have determined that a given sample may be erroneous if it deviates unexpectedly from adjacent samples. The system may give the listener the opportunity to correct the possibly erroneous sample.

Additionally, the system may determine that the listener's hearing is severely damaged at specific ranges of frequencies if the difference between adjacent samples is significant, especially if said difference is consistent between multiple tests. In such cases, the system may notify the listener of the results, but will not attempt to adjust for this damage (which would create an-natural "notch" in the correction curve as described later).

In certain embodiment, the system may further in step 225 enable the user to create and name a "profile" 120, a representation of their test results. The profile may be formatted as follows:

u:2A17H8,d:92DWA9,i:162,a:059800,f:011300,c:056560,r:033800,p1000

020:007800, pr000020:007910,p1012000:007800, pr057850:057996# where: u=user ID; d=device ID; i=user score; a=maximum amplitude; f=audible frequency floor; c=audible frequency ceiling; r=relative volume of 2 k reference frequency; p(l,r)xxxxxx=relative volume of specified frequency and ear (left or right); #=end of file. In the example shown, the user and device ID's are 6 digit alphanumeric combinations accommodating over one billion unique users. All other values are 16 bit integers, with a leading zero. The device ID is only known if the user tests with a known output device. If so, the user's profile is considered "device independent" and can be reverse engineered to any other known device. If the device ID was not known and indicated, its ID is stored as 000000.

The system may also report the results of the listener's test to a data repository 116 for display and analysis. The listener may be required to allow this reporting to use the system, or the listener may be allowed to opt-out of said data collection. The profile may be saved to the local storage of the user computing device. In the alternative or in addition, the profile may be transmitted to and saved on the host server accessible via the communications network.

In one embodiment, and with further illustrative reference to FIG. 4, when the listener is done testing the system may generate a mathematical equation representing a parametric curve between the accepted sample points. This curve may be visually represented to the listener 416. The listener may be instructed to name and save this correction, or curve 416. For example, the system may suggest the correction be named after the listener and the speaker or headphones used for the test.

The listener may now use the system to listen to any recording 118 on that audio device with a transform equation representing the correction curve 416 applied to the audio signal. This correction is performed in real time by inverting the curve 416 and applying it to the signal. Additionally, the system may allow the user to apply other transformations to the audio signal either before or after the correction curve 416 in order to further improve sound reproduction. Examples of such transformations may include dithering the data to higher sample rates, removing digital compression artifacts, normalizing volume levels, expanding or compressing dynamic range, or any other transformation to the audio signal.

On devices that support the creation of audio recordings, the listener may choose to permanently apply the correction curve 416 to the audio recording. The listener may choose to overwrite the existing recording, or to make a new recording 122.

Figure 3:
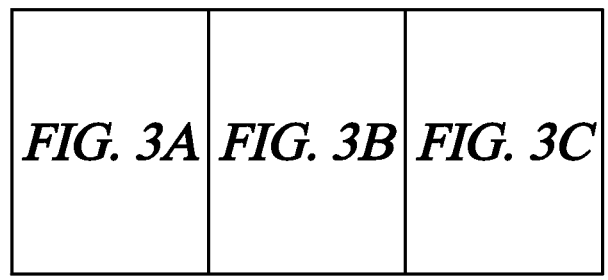
FIGS. 3A, 3B and 3C include a flowchart representing an embodiment of a signal processing method according to the present disclosure.
Figure 3A:
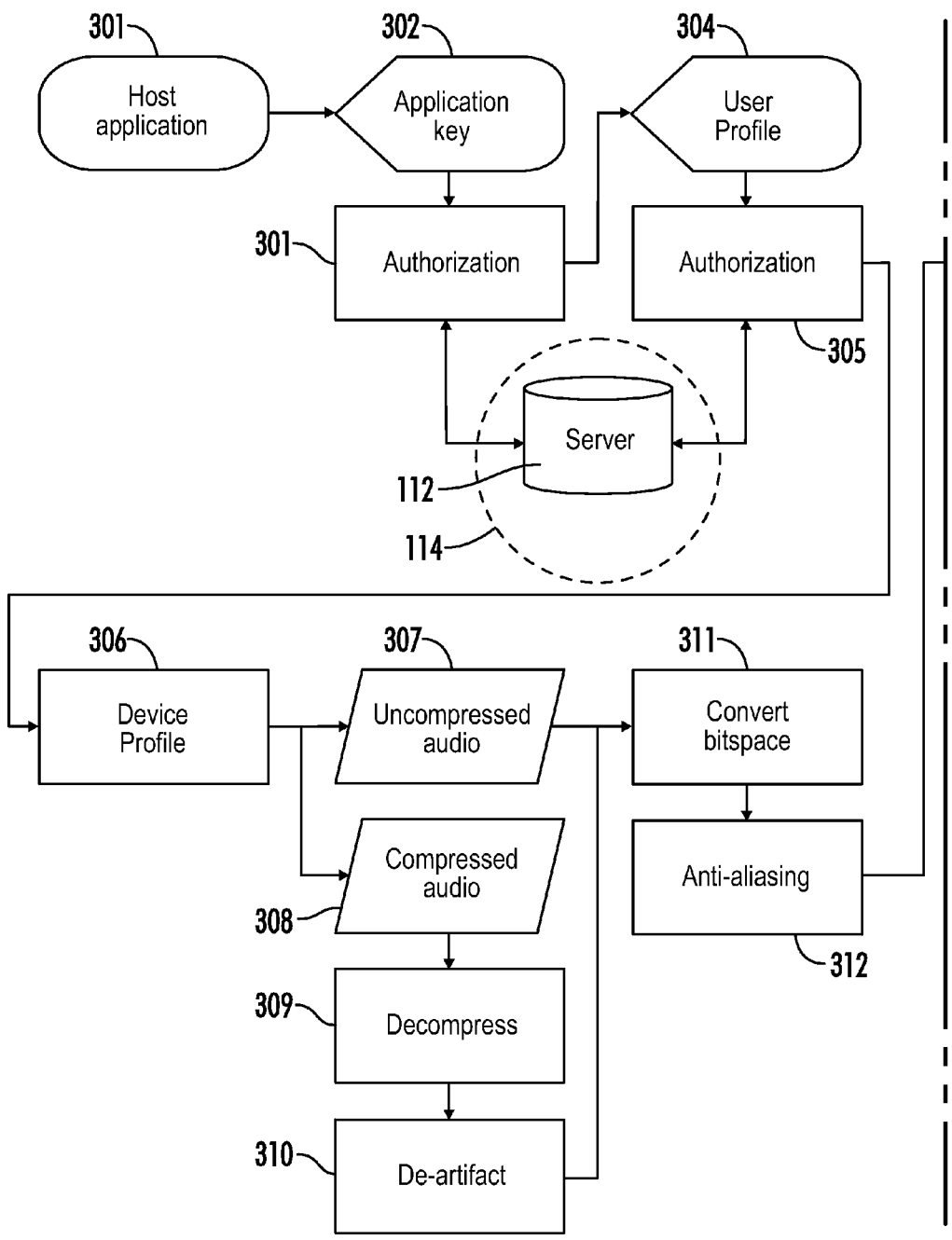
Figure 3B:
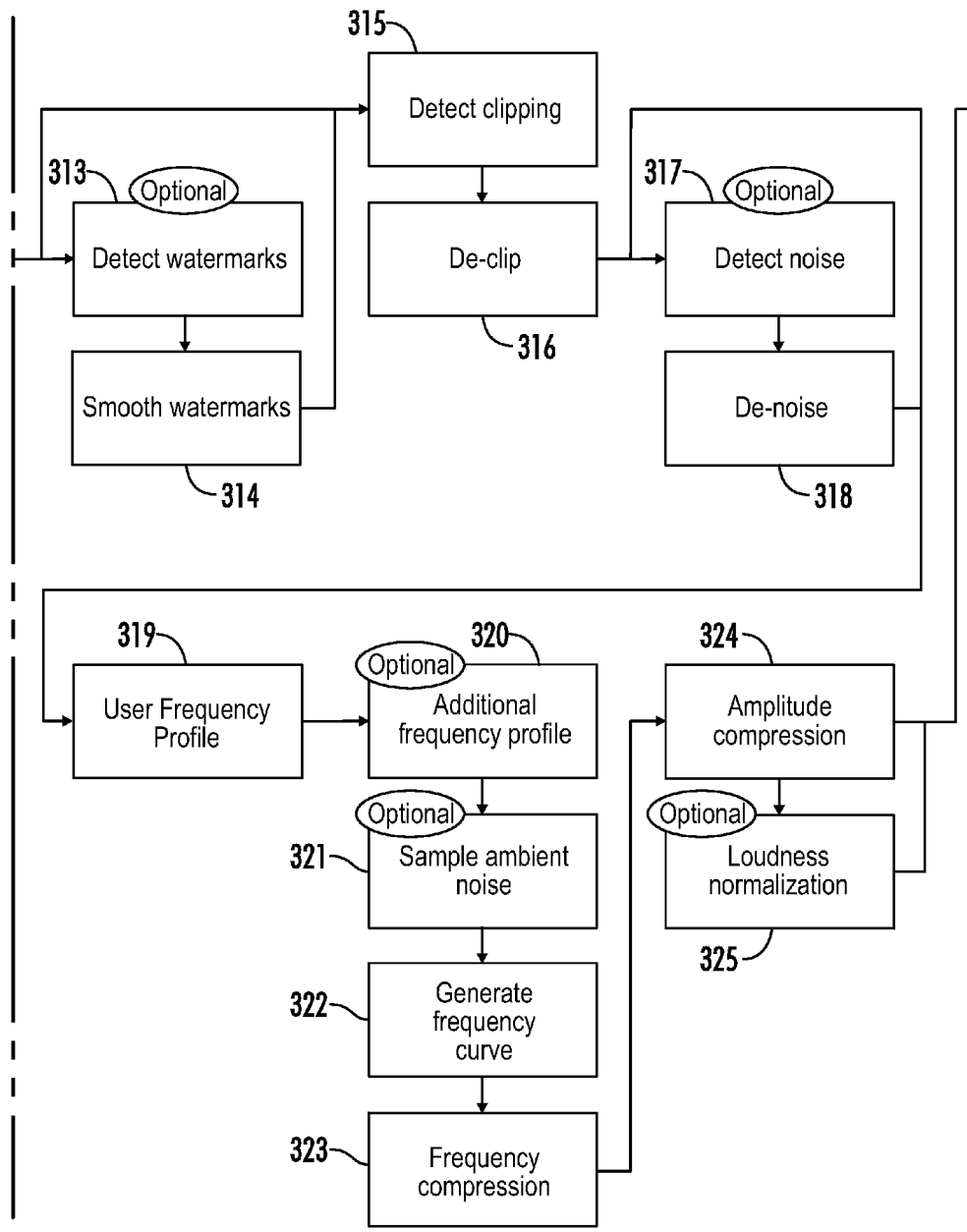
Figure 3C:
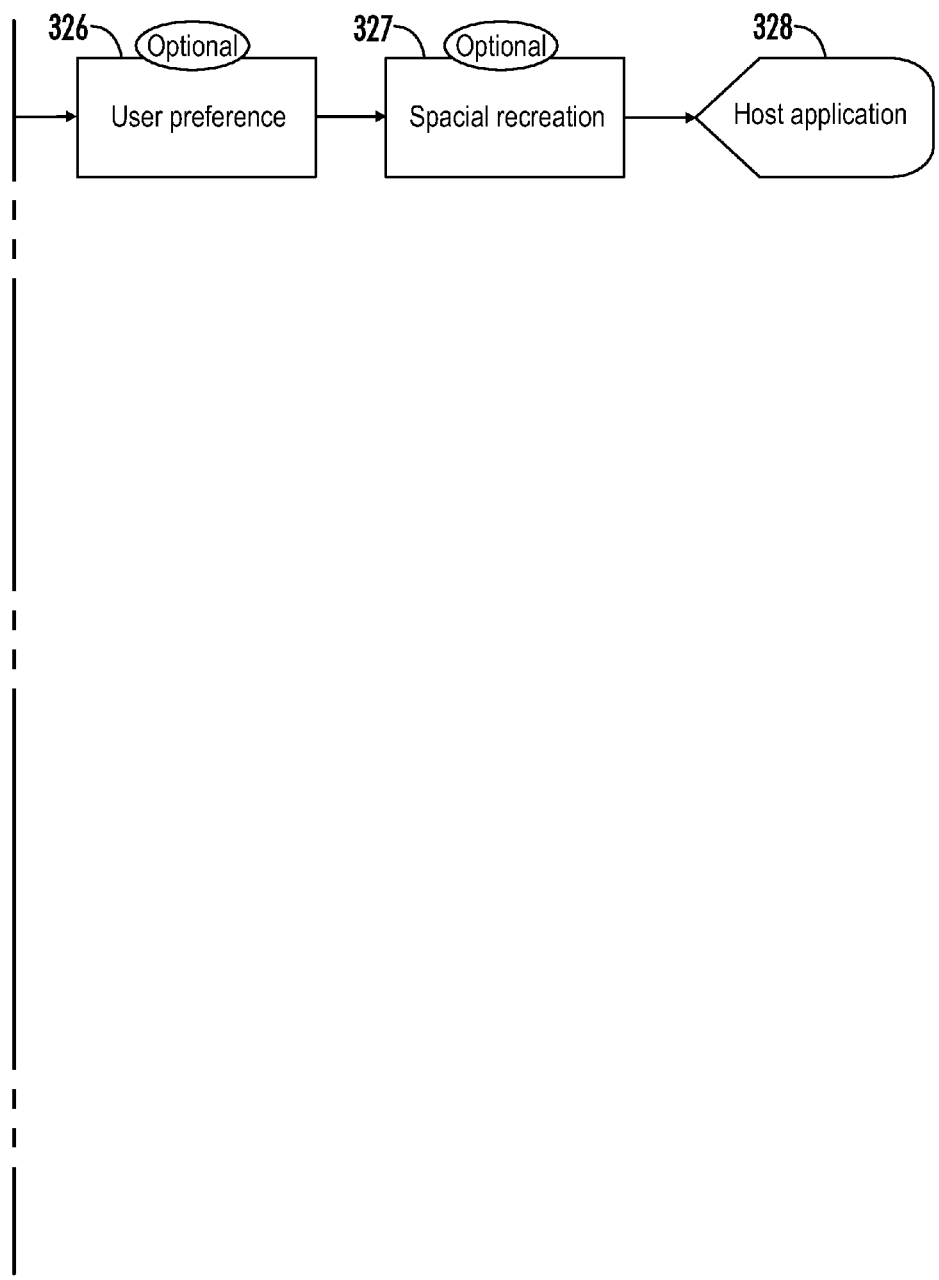

With further reference now to FIGS. 3A, 3B and 3C, in an embodiment the system may conduct signal processing and reproduction according to an exemplary method 300 as follows. Generally stated, various embodiments of the method 300 preferably generate and apply a transform equation representative of a correction curve to correct for deficiencies in the source material, the delivery medium, ambient noise, the output device and the user's hearing in one process.

In accordance with step 301, a "host" application executed on the user's hardware device is pre-compiled with a digital signal processing "plug-in" which is serialized uniquely to each host application.

The host application passes a key to the plug-in to verify that it is allowed to utilize the plug-in (step 302). The key is unique to the host application, and the plug-in validates the key against its serialization. If the key validates, then the plug-in determines if the host license is valid. The plug-in further (in step 303) attempts to communicate with an authorization server (e.g., the host server 112) via a communications network 114. If the plug-in can communicate with the authorization server, and the host application's license is valid, then the plug-in returns a success code to the host, and stores the success code and timestamp locally to the user's hardware device. Alternatively, if the plug-in can communicate with the authorization server, but the host's license is not valid, then the plug-in returns an error code to the host. If the plug-in cannot communicate with the authorization server, and there is no recent license validation stored on the user's hardware device, then the plug-in returns an error code to the host application. Alternatively, if the plug-in cannot communicate with the authorization server, and there is a recent license validation stored on the user's hardware device, then the plug-in returns a success code to the host application. If the key does not validate, the plug-in returns an error code to the host application.

The host application passes the identification code for the user's hearing "user profile" 120 created in accordance with the testing phase 200 to the plug-in (step 304). The plug-in validates the host application's permission to use the user profile, and attempts to communicate with the authorization server (step 305). If the plug-in can communicate with the authorization server, and if the user has approved the host application to use their user profile, then the plug-in returns a success code to the host application and stores the success code and timestamp locally to the user's hardware device. If the user has not yet approved the host application to use their user profile, a request to approve the host application may be displayed to the user. However, if the user has denied permission to the host application to use their user profile then an error code may be instead returned to the host application. If the plug-in cannot communicate with the authorization server, and if there is a recent success code stored on the user's hardware device, then the plug-in returns the success code to the host application. If there is no recent success code stored on the user's hardware device, then the plug-in returns an error code to the host application.

In accordance with step 306, the host application in various embodiments may indicate a "device profile" to the plug-in. The available processing power of the audio output device is profiled and this information is used to determine the amount and quality of real time processing. For example, the output device characteristics may be implemented to adjust for the lowest and highest frequencies that the output device(s) can reproduce, and further to adjust for the maximum amplitude that the device can reproduce without distortion. In an embodiment, for low profiles (wherein the device may be considered to have very limited processing power) and for standard or main profiles (average processing power), signals may be buffered in memory with 16 bits of resolution, and a 44.1 khz sample rate. High, or maximum, profile devices may alternatively utilize up to 96 khz/24 bit processing. Subsequent transformations may utilize floating point operations.

In accordance with steps 307-310, the host application indicates the type of audio data it is passing to the plug-in, for example, whether the format of audio data is uncompressed (or raw) or compressed, and further the type of compression (e.g., MP3, AAC, etc.). The host application may indicate the method of delivery for the audio data, such as for example, whether the data is to be delivered as a complete file, as a data stream, etc.

If the format of the audio data is compressed, it may in an embodiment be decompressed via one or more methods as appropriate for the particular method of compression (step 309). Depending on the device profile, the method of decompression can be biased towards efficiency or quality.

Further depending on the method of compression, known compression artifacts may be removed or mitigated (step 310). Examples of such artifacts are, but are not limited to: macro blocking; inter-sample peaks; pre-echo; joint stereo flanging and the like.

In accordance with step 311, the audio data's native bitspace (sample rate and bit depth) may be converted, if necessary, to the native bitspace of the plugin. The native bitspace of the plugin can vary depending on the device profile, but if possible the plug-in attempts to perform all subsequent operations in a bitspace twice that intended for output (so the output can be super-sampled).

In accordance with step 312, if the native data is to be increased, it can be anti-aliased utilizing techniques biased towards efficiency or quality depending on the device profile, such as, but not limited to nearest neighbor, linear, and cubic transformations.

In accordance with step 313, the system may further determine whether the audio data may be "watermarked" with a spread spectrum signature at the time of creation. While intended to be inaudible, sometimes this watermarking is applied in so aggressive a manner as to be audible. Depending on user preference, the plug-in can detect energy pulses in regular blocks and smooth these pulses. One possible example of such watermarking divides the audio data into 0.08 second blocks. Each block is divided in two: some amount of energy is added to the first half and the same amount is subtracted from the second half. The plug-in detects this modulation and attempts to mitigate (smooth) it (step 314).

The plug-in may further analyze the audio data for artificial amplitude "peaks" (clipping) in the signal (step 315). When clipped peaks are found, the plug-in "rolls-off" the peak, reducing the amplitude with a logarithmic curve to simulate an analog peak (step 316).

Based on user preference, the plug-in may seek to detect (step 317) and mitigate (step 318) either analog or digital noise encoded in the audio data. The plug-in stores "precomputed" samples of known noise. Examples of such are, but are not limited to: tape hiss; electrical hum; dithering and the like. The plug-in compares the audio data against these known noise samples, based on a variable, possibly user controlled, tolerance. If the plug-in detects a match with a known noise sample, the plug-in removes the noise from the data. Depending on the device profile, the method of removal may prioritize efficiency (a simple bitwise XOR) or quality (gates, expanders, etc.).

Measured data from the previously created user profile 120 may be combined with other parameters to manipulate the frequency response of the audio data (step 319). The volume difference of each tested frequency point for each channel may be applied relative to the reference point of 2 kHz, which is typically the midpoint, or no adjustment.

In some embodiments, the measured data from another individual's profile is added to the user profile data to compute a new volume difference for that frequency point for each channel (step 320).

In some embodiments, the user computing device may be used to sample ambient (external) audio levels (step 321). A full-spectrum microphone such as that built into the user device may for example be used to sample the ambient soundscape. If ambient sound levels exceed a certain, possibly user defined, threshold, then those frequency points that exceed that threshold are adjusted accordingly. For example, the transition between the frequencies to be adjusted and surrounding frequencies may be logarithmically "rolled off" to integrate the adjustment naturalistically.

At this point all possible adjustments to individual frequency points for each channel have preferably been combined into the final value for each frequency point. The lowest sampled frequency below the measured frequency floor in the user profile is set to zero, the highest sampled frequency above the measured frequency floor in the user profile is set to zero, and a curve is calculated to represent the frequency correction required for all sampled frequencies, including the frequencies between the tested frequencies (step 322). Depending on the device profile, the method for calculating the curve may prioritize efficiency (e.g., linear) or quality (e.g., bezier, b-spline, fractal).

The frequency response of the audio data may be adjusted according to the curve's computed values for each frequency sample point.

In accordance with step 323, the total range of sampled frequencies in the audio data may be compared against the range of audible frequencies based on the user profile. In certain embodiments, the total frequency range is compressed to fit within the audible frequency range. In a conventional system, single band or simple multi band compression would be used. In contrast, systems and methods as disclosed herein may implement a non-linear and logarithmic "S" curve to calculate the compression in order to yield more naturalistic results. The frequency midpoint is unaffected by the adjustment, while the measured frequency floor ("knee") and frequency ceiling ("shoulder") are progressively affected by the adjustment. Frequencies are adjusted between the knee and shoulder based on the calculated curve.

In accordance with step 324, the total possible maximum amplitude in the audio data may be compared against the measured maximum amplitude stored in the user profile. In certain embodiments, the total amplitude "dynamic range" is compressed to fit within the measured maximum dynamic range. In a conventional system, the signal may typically be compressed equally across all amplitude levels. Instead, various embodiments of a system as disclosed herein implement a curve to calculate compression in order to yield more naturalistic results. The amplitude midpoint is unaffected by the adjustment, while the measured amplitude ceiling ("shoulder") is most affected (100%) by the adjustment.

In certain embodiments, the user may elect to have "loudness correction" applied to the amplitude curve (step 325). An amplitude "knee" is determined based on the difference between the software volume at the time of the correction and the software volume stored in the user profile. Amplitude is adjusted between the knee and shoulder based on the calculated curve.

In certain embodiments, the user may decide to apply any number of additional signal operations to the audio data (step 326). These operations may be based on native capabilities of the plug-in, such as, but not limited to, a user adjustable equalizer. These operations may be performed by auxiliary operators that act upon and return the audio data to the plug-in. Based on the device profile, these operations may be performed in a manner that biases towards efficiency or quality. Optionally, the user may elect to modify the order in which these additional operations are performed.

In certain embodiments, the user may decide to correct the stereo imaging of the audio data (step 327). In conventional applications, commercially produced music is mixed and mastered for playback on loudspeakers placed an equal distance apart and in front of the listener. This presents a problem for the user when listening to music on either headphones, or in their car. When a stereo mix is experienced over headphones, all instruments or voices in that piece get placed in between the listener's ears, or otherwise stated inside of their head, an effect which is not only unnatural and fatiguing for the listener, but undermines the original instrument placement. It disturbs the spatialization of the music and makes the sound image appear as three isolated lobes inside of the listener's head.

Similarly, when a stereo mix is experienced in an automobile cabin, the extreme positioning of the driver ensures that the original placement of the instruments is lost, and the stereo soundscape is destroyed. Simply adjusting the relative volume of the left and right channels (balance) may be insufficient to correct this problem.

In accordance with an embodiment of a system as disclosed herein, additional channels may be created from the left and right stereo channels, wherein the new channels contain only the data unique to each source channel. The creation of these new channels avoids audible "comb filtering" artifacts created by simpler techniques. Depending on the listening environment indicated by the user, the difference between each source channel may be mixed into the opposite source channel at an amount and with a delay appropriate to correct for the difference between the user's listening environment and the theoretical ideal listening environment (two speakers equidistant from each other, six feet in front of the user). Spectral (frequency) alterations may be made to correct for errors introduced by cross feeding channels. Examples of environments that can be corrected include, but are not limited to: headphones (wherein the "phantom" center channel is perceived to move from inside the user's head to in front of the user); or an automobile cabin (wherein the "phantom" center channel is perceived to move from far to the right of the user to directly in front of the user).

In certain embodiments, the new audio data may be delivered to the host application for presentation to the user (step 328). The audio data may be presented as a complete file or streamed, depending on how the audio data was provided to the plug-in.

In view of the teachings presented above, one of skill in the art may readily appreciate additional or alternative embodiments of a system and method as disclosed herein for generating and experiencing near perfect audio reproduction across the entire spectrum of audible frequencies at the exact same reference volume level intended by audio engineers.

The individual originating an audio recording (such as the artist or engineer) may create or implement a profile that is embedded or otherwise included alongside the recording, such as for example as metadata associated with an executable audio file. Additionally, output devices, such as headphones or speakers, may include or otherwise be associated with a profile specific to the respective device. A user profile is typically only valid for a single output chain (most importantly, a given output device and a given set of ears). Unless the speakers, headphones or the like as used during testing have an associated profile, a new test must be performed for each output device (a user's car system, for example).

Accordingly, a profile according to embodiments as disclosed herein represents that which is unique to the tested user or device, and does not typically represent JIT (Just In Time) corrections such as restoring recording deficits or adjusting for ambient noise.

In certain embodiments, the user may be enabled to share a profile with other users—either other users associated with the same host system, or with complimentary services and devices (such as streaming music services, or embedded devices). For example, by including the user profile of the artist or engineer that recorded the song in metadata associated with the audio file, a very accurate reproduction of the original intent can be preserved and transported for playback by other users having authorization via the host system.

Similarly, this system methodology could be used to calibrate color hue, saturation and brightness for personal computers, tablets, gaming consoles, smartphones, televisions and home theaters. Individuals could calibrate their personal screens and televisions to match the intended experience of the developers of graphic design programs, applications, video game consoles, icons or movie auteurs.

Additionally, with the increasing proliferation of computing eyewear—such as Google Glass—individuals could employ the proposed system methodology to derive and apply a customized parametric curve to their own personal eyewear that compensates for photoreceptor color cone degradation. In much the same way that optometry applies customized lenses to the individual eye to improve focus the proposed system may apply a parametric curve to "smart eyewear" to improve or restore the depth and vibrancy of color perception impaired by age or congenital defect.

In addition to headphones, personal stereos, home and auto stereos and portable audio devices, the system may also be used to calibrate optimal sound reproduction of smart televisions and connected home 5.1, 7.1 and other surround sound speaker configurations.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may.

Also, unless indicated otherwise from the context of its use herein, the terms "known," "fixed," "given," "certain" and "predetermined" generally refer to a value, quantity, parameter, constraint, condition, state, process, procedure, method, practice, or combination thereof that is, in theory, variable, but is typically set in advance and not varied thereafter when in use.

Terms such as "providing," "processing," "supplying," "determining," "calculating" or the like may refer at least to an action of a computer system, computer program, signal processor, logic or alternative analog or digital electronic device that may be transformative of signals represented as physical quantities, whether automatically or manually initiated.

Depending on the embodiment, certain acts, events, or functions of any of the algorithms described herein can be performed in a different sequence, can be added, merged, or left out altogether (e.g., not all described acts or events are necessary for the practice of the algorithm). Moreover, in certain embodiments, acts or events can be performed concurrently, e.g., through multi-threaded processing, interrupt processing, or multiple processors or processor cores or on other parallel architectures, rather than sequentially.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable medium known in the art. An exemplary computer-readable medium can be coupled to the processor such that the processor can read information from, and write information to, the memory/ storage medium. In the alternative, the medium can be integral to the processor. The processor and the medium can reside in an ASIC. The ASIC can reside in a user terminal. In the alternative, the processor and the medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The previous detailed description has been provided for the purposes of illustration and description. Thus, although there have been described particular embodiments of a new and useful invention, it is not intended that such references be construed as limitations upon the scope of this invention except as set forth in the following claims.

What is claimed is:

1. A non-transitory computer readable medium functionally linked to an audio output device configured to produce audio output responsive to audio input signals, the computer readable medium having program instructions residing thereon and executable by a processor to direct the performance of operations comprising:
   upon initiation of an auditory calibration procedure having one or more components for mitigating anticipation and assumption by a user,
      identifying a first volume level as a minimum volume level at which a tone having a nominal frequency is audible to the user,
      identifying a minimum frequency at which a tone at said first volume level is audible to the user,
      identifying a maximum frequency at which the tone at said first volume level is audible to the user,
      for each of one or more samples having frequencies between said minimum frequency and said maximum frequency, determining a minimum volume level at which a respective frequency is audible to the user; and
   upon completion of the auditory calibration procedure, generating a transform equation representing a customized parametric correction curve based on the minimum volume levels at the one or more sample frequencies, and
   responsive to real time audio signals generated upon execution of an audio file functionally linked to the processor,
      applying the correction curve to modify the real time audio signals,
      further modifying the real time audio signals with transformations based on a profile for the audio output device, and
      further modifying the real time audio signals with logarithmic transformations to reduce artificial amplitude peaks and sampled ambient sound frequencies exceeding a predefined threshold,
      wherein the modified real time audio signals are provided as audio input signals to the audio output device.

2. The computer readable medium of claim 1, wherein the operation of identifying a first volume level as a minimum volume level at which a tone having a nominal frequency is audible to a user comprises:
   sweeping a first audio tone having a nominal frequency from a minimum volume level toward a maximum volume level,
   receiving user input from a user interface functionally linked to the processor, the user input indicating the minimum volume level at which the first audio tone is audible to the user, and
   storing the minimum volume level at which the first audio tone is audible to the user in memory as the first volume level.

3. The computer readable medium of claim 2, wherein for each of one or more samples, determining a minimum volume level at which a respective frequency is audible to the user comprises:

sweeping an audio tone at the respective frequency from a minimum volume level toward a maximum volume level, receiving user input from the user interface indicating the minimum volume level at which the audio tone is audible to the user, and storing the minimum volume level at which the audio tone is audible to the user in memory and in association with the respective frequency.

4. The computer readable medium of claim 3, wherein identifying a minimum frequency at which a tone at said first volume level is audible to the user comprises:

sweeping an audio tone at the first volume level from a minimum audible frequency toward a maximum audible frequency, receiving user input from the user interface indicating the minimum frequency at which the audio tone is audible to the user, and storing the minimum frequency at which the audio tone is audible to the user in memory.

5. The computer readable medium of claim 4, wherein identifying a maximum frequency at which a tone at said first volume level is audible to the user comprises:

sweeping an audio tone at the first volume level from the maximum audible frequency toward the minimum audible frequency, receiving user input from the user interface indicating the maximum frequency at which the audio tone is audible to the user, and storing the maximum frequency at which the audio tone is audible to the user in memory.

6. The computer readable medium of claim 1, wherein the program instructions are further executable to identify outlier samples with respect to the correction curve, and to recommend to the user via the user interface that the test be repeated for one or more of the identified outlier samples.

7. The computer readable medium of claim 1, wherein the auditory calibration procedure is independently conducted for each of the user's left and right ears.

8. The computer readable medium of claim 1, wherein the program instructions are further executable to direct the performance of storing a user profile in memory comprising the transform equation, wherein said user profile is subsequently retrievable for application with respect to audio signals from any of one or more executable audio files functionally linked to the processor.

9. The computer readable medium of claim 8, wherein the user profile is stored in association with the audio output device as a first audio output device, further wherein a separate auditory calibration procedure is required of the user for modification of audio signals to any one or more additional audio output devices.

10. The computer readable medium of claim 1, wherein the program instructions are further executable to apply additional transformations to the real time audio signals either or both of before the correction curve represented by the transform equation and after the correction curve represented by the transform equation, said additional transformations comprising detecting noise by comparing the real time audio signals against known noise samples, based on a predetermined tolerance, and removing the detected noise, wherein the known noise samples comprise one or more of tape hiss, electrical hum and dithering data associated with the user to higher sample rates.

11. The computer readable medium of claim 1, wherein the program instructions are further executable to apply additional transformations to the real time audio signals either or both of before the correction curve and after the correction curve, said additional transformations comprising removing digital compression artifacts.

12. The computer readable medium of claim 1, wherein the program instructions are further executable to apply additional transformations to the real time audio signals either or both of before the correction curve and after the correction curve, said additional transformations comprising expanding or compressing a maximum range of relative volume amplitude.

13. The computer readable medium of claim 1, wherein the program instructions are further executable to direct the performance of one or more operations comprising:

compressing a total range of sampled frequencies in the audio data to fit within a range of audible frequencies associated with the transform equation, and compressing a total possible maximum amplitude in the audio data to fit within a measured maximum amplitude associated with the transform equation.

14. A system comprising:

an audio output device configured to produce audio output responsive to audio input signals;

a display unit;

data storage media upon which resides an audio file and metadata corresponding to a first user, the metadata further comprising a transform equation representing a customized parametric correction curve based on each of a first volume level as a minimum volume level at which a tone having a nominal frequency is audible to the first user, a minimum frequency at which a tone at said first volume level is audible to the first user, a maximum frequency at which the tone at said first volume level is audible to the first user, and for each of one or more samples having frequencies between said minimum frequency and said maximum frequency, a minimum volume level at which a respective frequency is audible to the first user;

a processor configured upon selective execution of the audio file to further apply the transform equation to modify real time audio signals associated with the audio file, further modify the real time audio signals with transformations based on a profile for the audio output device, and further modify the real time audio signals with logarithmic transformations to reduce artificial amplitude peaks and sampled ambient sound frequencies exceeding a predefined threshold, and provide the modified real time audio signals as audio input signals to the audio output device.

15. The system of claim 14, wherein the data storage media comprises the metadata as a first metadata set stored in association with the audio output device as a first audio output device, and further comprises a second metadata set for selective execution alongside the audio file and in association with a second audio output device.

16. The system of claim 14, wherein the processor is further configured to apply additional transformations to the real time audio signals either or both of before the correction curve represented by the transform equation and after the correction curve represented by the transform equation, said additional transformations comprising detecting noise by comparing the real time audio signals against known noise samples, based on a predetermined tolerance, and removing the detected noise, wherein the known noise samples comprise one or more of tape hiss, electrical hum and dithering data associated with the user to higher sample rates.

17. The system of claim 14, wherein the processor is further configured to apply additional transformations to the real time audio signals either or both of before the correction curve represented by the transform equation and after the correction curve represented by the transform equation, said additional transformations comprising removing digital compression artifacts.

18. The system of claim 14, wherein the processor is further configured to apply additional transformations to the real time audio signals either or both of before the correction curve represented by the transform equation and after the correction curve represented by the transform equation, said additional transformations comprising expanding or compressing a maximum range of relative volume amplitude.

19. A method of calibrating and reproducing real time audio signals based on an auditory signature of a user, the method comprising:

for a particular audio output device, (a) identifying a first volume level as a minimum volume level at which a tone having a nominal frequency is audible to the user;

(b) identifying a minimum frequency at which a tone at said first volume level is audible to the user;

(c) identifying a maximum frequency at which the tone at said first volume level is audible to the user;

(d) for each of one or more samples having frequencies between said minimum frequency and said maximum frequency, determining a minimum volume level at which a respective frequency is audible to the user;

generating a user profile associated with the audio output device and comprising a transform equation representing a customized parametric correction curve based on the minimum volume levels at each of the nominal frequency, the minimum frequency, the maximum frequency and the one or more sample frequencies;

applying the transform equation to modify real time audio signals generated upon execution of an audio file;

further modifying the real time audio signals with transformations based on a device profile for the audio output device, and further modifying the real time audio signals with logarithmic transformations to reduce artificial amplitude peaks and sampled ambient sound frequencies exceeding a predefined threshold, wherein the modified real time audio signals are provided as audio input signals to the audio output device.

20. The method of claim 19, wherein the audio output device comprises a first audio device, the method further comprising repeating each of sub-steps (a) to (d) and generating a corresponding user profile with respect to a second audio device.

* * * * *